US010293199B2

(12) United States Patent
Roh et al.

(10) Patent No.: US 10,293,199 B2
(45) Date of Patent: May 21, 2019

(54) REHABILITATION TRAINING APPARATUS

(71) Applicant: NEOFECT CO., LTD., Yongin-si, Gyeonggi-do (KR)

(72) Inventors: Sung Jun Roh, Seoul (KR); Hyun Soo Kim, Seoul (KR); Soo Bin Lee, Seongnam-si (KR); Ho Yeong Song, Yongin-si (KR); Ho Young Ban, Yongin-si (KR); Young Geun Choi, Yongin-si (KR); Dae Hoon Jang, Guri-si (KR); Byeong Geol Park, Icheon-si (KR); Kyung Hwan Yoo, Incheon (KR)

(73) Assignee: NEOFECT CO., LTD., Yongin-si (KR)

(*) Notice: Subject to any disclaimer, the term of this patent is extended or adjusted under 35 U.S.C. 154(b) by 0 days.

(21) Appl. No.: 15/827,555

(22) Filed: Nov. 30, 2017

(65) Prior Publication Data

US 2018/0078814 A1    Mar. 22, 2018

Related U.S. Application Data

(63) Continuation of application No. PCT/KR2017/005491, filed on May 26, 2017.

(30) Foreign Application Priority Data

May 27, 2016   (KR) .................. 10-2016-0065439
May 22, 2017   (KR) .................. 10-2017-0062704

(51) Int. Cl.
*A63B 22/00*   (2006.01)
*A63B 23/12*   (2006.01)
(Continued)

(52) U.S. Cl.
CPC ...... *A63B 21/00181* (2013.01); *A61B 5/1124* (2013.01); *A61H 1/008* (2013.01);
(Continued)

(58) Field of Classification Search
None
See application file for complete search history.

(56) References Cited

U.S. PATENT DOCUMENTS 3,130,968 A * 4/1964 De Feen ............... A63B 23/00
                                                  297/344.13
3,421,760 A * 1/1969 Freeman, Jr. ......... A63B 21/04
                                                  482/130
(Continued)

FOREIGN PATENT DOCUMENTS

CN       2812998 Y      9/2006
CN     104606867 A      5/2015
(Continued)

OTHER PUBLICATIONS

International Search Report issued in PCT/KR2017/005491; dated Aug. 28, 2017.
(Continued)

*Primary Examiner* — Stephen R Crow
(74) *Attorney, Agent, or Firm* — Studebaker & Brackett PC

(57) ABSTRACT

Disclosed is a rehabilitation training apparatus. The rehabilitation training apparatus includes a pair of first tracks that are arranged in parallel at an interval, a second track movably connected to the pair of first tracks, a hand holder that is movably provided in the second track and on which a hand and an arm of a user is held, and a stopper for a track provided in at least one of the first tracks and the second track to limit movements of the second track and the hand holder.

15 Claims, 7 Drawing Sheets

(51) Int. Cl.
| | |
|---|---|
| *A63B 21/00* | (2006.01) |
| *A61H 1/02* | (2006.01) |
| *A61B 5/11* | (2006.01) |
| *A63B 24/00* | (2006.01) |
| *A61H 1/00* | (2006.01) |
| *A63B 22/20* | (2006.01) |
| *A63B 23/035* | (2006.01) |
| *A63B 23/14* | (2006.01) |
| *A63B 71/06* | (2006.01) |
| *A63B 21/005* | (2006.01) |
| *A63B 71/00* | (2006.01) |
| *A63B 21/02* | (2006.01) |
| *A61B 5/00* | (2006.01) |

(52) U.S. Cl.
CPC ......... *A61H 1/0274* (2013.01); *A61H 1/0281* (2013.01); *A63B 21/00* (2013.01); *A63B 21/00178* (2013.01); *A63B 21/4035* (2015.10); *A63B 21/4045* (2015.10); *A63B 22/20* (2013.01); *A63B 23/035* (2013.01); *A63B 23/12* (2013.01); *A63B 23/14* (2013.01); *A63B 24/00* (2013.01); *A63B 24/0087* (2013.01); *A61B 5/4528* (2013.01); *A61B 2505/09* (2013.01); *A61H 1/0285* (2013.01); *A61H 2201/018* (2013.01); *A61H 2201/123* (2013.01); *A61H 2201/1207* (2013.01); *A61H 2201/149* (2013.01); *A61H 2201/1635* (2013.01); *A61H 2201/1638* (2013.01); *A61H 2201/1664* (2013.01); *A61H 2201/1666* (2013.01); *A61H 2201/5007* (2013.01); *A61H 2201/5043* (2013.01); *A61H 2201/5061* (2013.01); *A61H 2201/5064* (2013.01); *A61H 2201/5092* (2013.01); *A61H 2205/062* (2013.01); *A61H 2205/065* (2013.01); *A63B 21/0058* (2013.01); *A63B 21/02* (2013.01); *A63B 21/4043* (2015.10); *A63B 22/203* (2013.01); *A63B 23/1245* (2013.01); *A63B 23/1254* (2013.01); *A63B 71/0622* (2013.01); *A63B 2022/0094* (2013.01); *A63B 2024/0093* (2013.01); *A63B 2071/0072* (2013.01); *A63B 2220/10* (2013.01); *A63B 2220/13* (2013.01); *A63B 2220/51* (2013.01); *A63B 2220/805* (2013.01)

(56) References Cited

U.S. PATENT DOCUMENTS

| | | | | |
|---|---|---|---|---|
| 3,582,069 | A * | 6/1971 | Flick | A63B 21/154 434/255 |
| 3,797,824 | A * | 3/1974 | Osbourne | A63B 22/203 482/132 |
| 4,886,050 | A * | 12/1989 | Iams | A63B 23/0355 434/255 |
| 5,224,909 | A * | 7/1993 | Hamilton | A63B 21/154 482/51 |
| 7,438,673 | B1 * | 10/2008 | Jones | A63B 22/203 482/51 |
| 7,931,570 | B2 * | 4/2011 | Hoffman | A63B 21/055 482/123 |
| 8,137,251 | B2 * | 3/2012 | Tozzi | A63B 22/203 482/132 |
| 9,011,296 | B2 * | 4/2015 | Peralo | A61H 1/02 482/123 |
| 9,630,056 | B2 * | 4/2017 | Rao | A63B 71/0054 |
| 2006/0040799 | A1 * | 2/2006 | Pompile | A63B 21/0552 482/92 |
| 2009/0105050 | A1 * | 4/2009 | Mayo | A63B 21/06 482/70 |
| 2010/0298097 | A1 * | 11/2010 | Preumont | A61H 1/0237 482/5 |
| 2012/0065030 | A1 | 3/2012 | Sandvig | |

FOREIGN PATENT DOCUMENTS

| | | |
|---|---|---|
| EP | 2 923 683 A1 | 9/2015 |
| KR | 10-2014-0044520 A | 4/2014 |
| KR | 10-2014-0130787 A | 11/2014 |
| KR | 10-2015-0083469 A | 7/2015 |
| KR | 10-2015-0118594 A | 10/2015 |
| WO | 2012/170815 A1 | 12/2012 |
| WO | 2015/144853 A1 | 10/2015 |

OTHER PUBLICATIONS

An Office Action issued by the Korean Patent Office dated Jun. 28, 2018, which corresponds to Korean Patent Application No. 10-2017-0062704 and is related to U.S. Appl. No. 15/827,555; with partial English language translation.

An Office Action issued by the Korean Patent Office dated Nov. 21, 2018, which corresponds to Korean Patent Application No. 10-2018-0135283 and is related to U.S. Appl. No. 15/827,555; with partial English language translation.

An Office Action; "Notice of Reasons for Refusal," issued by the Japanese dated Oct. 2, 2018, which corresponds to Japanese Patent Application No. 2017-563177 and is related to U.S. Appl. No. 15/827,555; with partial English language translation.

An Office Action issued by the Chinese Patent Office dated Dec. 3, 2018, which corresponds to Chinese Patent Application No. 201780001972.4 and is related to U.S. Appl. No. 15/827,555; with partial English language translation.

* cited by examiner

REHABILITATION TRAINING APPARATUS

CROSS-REFERENCE TO RELATED APPLICATIONS

The present application is a continuation of International Patent Application No. PCT/KR2017/005491, filed on May 26, 2017, which is based upon and claims the benefit of priority to Korean Patent Application Nos. 10-2016-0065439, filed on May 27, 2016 and 10-2017-0062704, filed on May 22, 2017. The disclosures of the above-listed applications are hereby incorporated by reference herein in their entirety.

BACKGROUND

Embodiments of the inventive concept described herein relate to a rehabilitation training apparatus, and more particularly to a rehabilitation training apparatus by which rehabilitation training of the joints of a wrist and a shoulder of the user can be performed.

In general, the joints of the human body are configured such that adjacent parts of the joints may be rotated about the joints.

Meanwhile, the aged persons or the patients with disability, whose muscular forces are weak, have difficulties in exercising their joints as compared with healthy persons, and it is substantially difficult to exercise with general sports equipment in spite of the needs of exercises.

In particular, because the patients who had surgical operations on the wrists and shoulders cannot exercise by themselves, the joints of the wrists and the shoulders may be stiff and hardened due to the weal muscles and insufficient supply of nutrients.

Accordingly, long-term rehabilitation training is necessary to prevent deformation of the joints and allow the patients to return to normal activities.

Meanwhile, most of the conventional rehabilitation apparatuses have only a function of constraining the angles of the joints of the wrists and the shoulders of the user to prevent excessive exercises, Accordingly, studies on the rehabilitation training apparatuses configured to change the angles of the joints with actuators have been made.

Accordingly, the applicant has developed a rehabilitation training apparatus that may allow the user to train the joint parts of the wrinkles and the shoulder by moving the hands and the arms of the user by using a fine muscular force while the hands are held and to perform rehabilitation training while conveniently setting an exercise range according to a body state of the user.

SUMMARY

Embodiments of the inventive concept provide a rehabilitation training apparatus by which the user may perform rehabilitation training while conveniently setting an exercise range according to the body state of the user and may perform rehabilitation training while changing the angles of the joints of the wrist and the shoulder of the user, by moving the hand and the arm by using the muscular force of the user.

Embodiments of the inventive concept also provide a rehabilitation training apparatus by which rehabilitation training may be performed by moving a hand holder in which a hand of the user is held according to characteristics of the user in various patterns and changing the angles of the joints of a wrist and a shoulder of the user.

In accordance with an aspect of the inventive concept, there is provided a rehabilitation training apparatus including a pair of first tracks that are arranged in parallel at an interval, a second track movably connected to the pair of first tracks, a hand holder that is movably provided in the second track and on which a hand and an arm of a user is held, and a stopper for a track provided in at least one of the first tracks and the second track to limit movements of the second track and the hand holder.

The stopper for a track may include a plurality of mounting grooves for a track formed in the pair of first tracks along a movement path of the second track at an interval, and a stopper pin for a track selectively mounted on the plurality of mounting grooves for a track to interrupt and release the movement path of the second track.

The stopper for a track may include a plurality of clips mounted on the pair of first tracks to interrupt and release the movement path of the second track.

The rehabilitation training system may further include a stopper for a holder provided in the second track to limit the movement of the hand holder.

The stopper for a holder may include a plurality of mounting grooves for a holder formed in the second track along the movement path of the hand holder at an interval, and a stopper pin for a holder selectively mounted on the plurality of mounting grooves for a holder to interrupt and release the movement path of the hand holder as an embodiment.

The stopper for a holder may include a plurality of clips mounted in the movement path of the hand holder of the second track to interrupt and release the movement path of the hand holder as another embodiment.

The rehabilitation training system may further include a board having a rectangular plate shape and forming an X-Y coordinate plane formed by the pair of first tracks and the second track.

The rehabilitation training system may further include a plurality of light emitting elements that emit light, and a plurality of light receiving elements that receive light emitted from the plurality of light emitting elements, and paths of the light, which are formed by the plurality of light emitting elements and the plurality of light receiving elements, may form an X-Y axis coordinate plane in the board while crossing each other.

The rehabilitation training system may further include a pointer provided on the hand holder to indicate a location of the hand holder on the X-Y axis coordinate plane of the board by interrupt the paths of the light.

The pointer may include a pointer tip that interrupts the paths of the light while moving along a plate surface of the board, a tip holder in which the pointer tip is accommodated to be elevated such that the pointer tip is attached to the plate surface of the board, and a mount that supports the tip holder on the hand holder.

The rehabilitation training may further include a communication module that transmits coordinate data obtained after the hand holder is moved to an external device.

The hand holder may include a holder body on which an arm of the user is held, a knob gripped by the hand of the user held on the holder body, a support bracket that supports the knob and the holder which are spaced apart from each other at an interval, and a guide pin for a holder coupled to the support bracket to guide the support bracket such that the support bracket reciprocates along the second track.

The rehabilitation training system may further include a slot formed in the support bracket, and a coupling member that couples the holder body to the slot such that the holder body is movable.

The rehabilitation training system may further include a pair of guide rails for a track arranged in the pair of first tracks along the pair of first tracks, and a pair of guide blocks for a track, to which the second track is connected, and which reciprocates along the pair of guide rails for a track.

The rehabilitation training system may further include a guide rail for a holder that is arranged along the second track, and a guide block for a holder connected to the hand holder to reciprocate along the hand guide rail.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
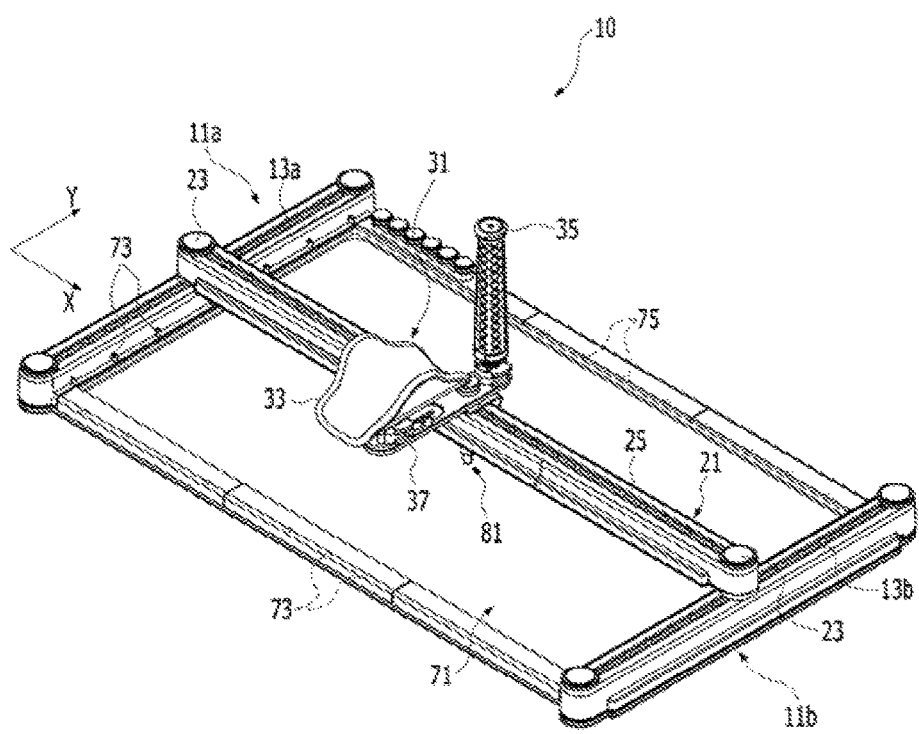
FIG. 1 is a perspective view of a rehabilitation training apparatus according to an embodiment of the inventive concept.
Figure 2:
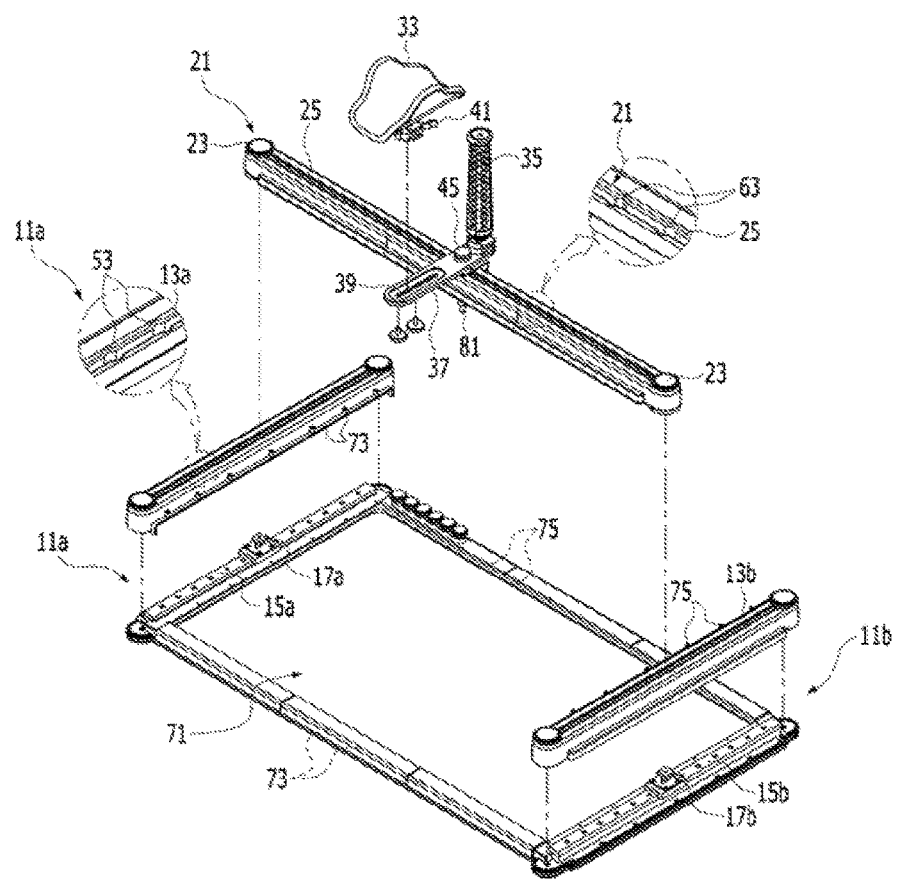
FIG. 2 is an exploded perspective view of FIG. 1.
Figure 3:
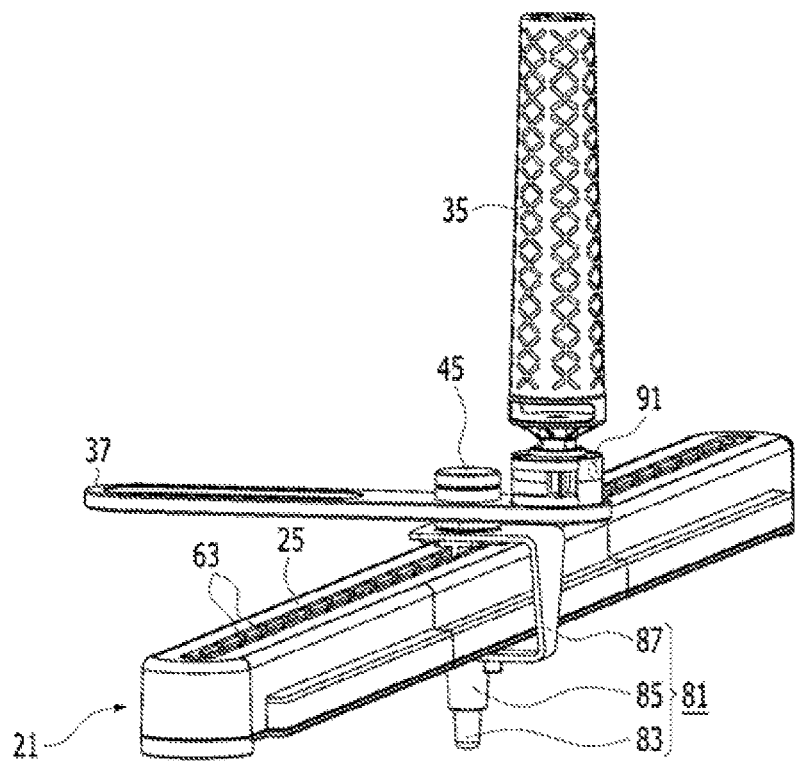
FIG. 3 is an enlarged perspective view of main parts of a second track and a hand holder of FIG. 1.
Figure 4:
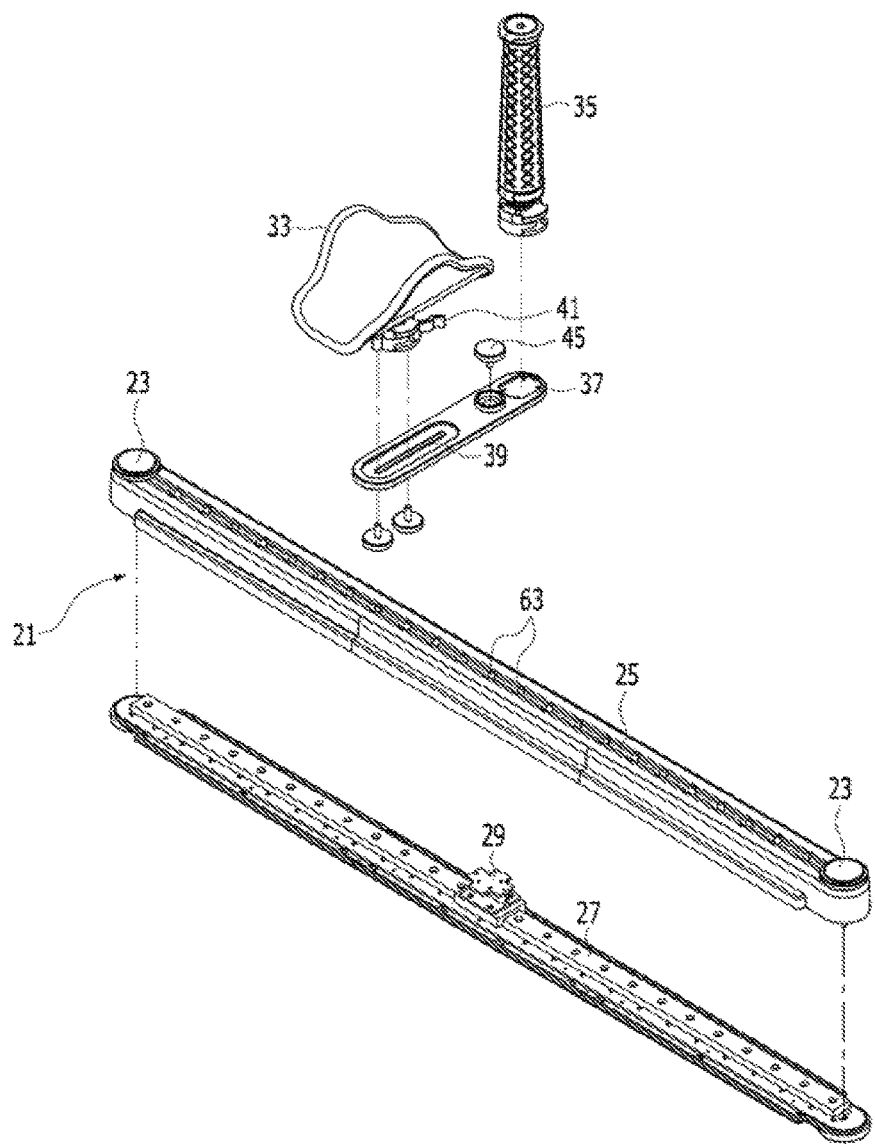
FIG. 4 is an exploded perspective view of a main part of the second track of FIG. 1.

Hereinafter, the inventive concept will be described in detail with reference to the accompanying drawings.

FIGS. 1 to 4 illustrate a rehabilitation training apparatus according to an embodiment of the inventive concept.

As illustrated in the drawings, the rehabilitation training apparatus 10 according to the embodiment of the inventive concept include a pair of first tracks 11a and 11b, a second track 21, a hand holder 31, and a stopper.

The pair of first tracks 11a and 11b have a hollow bar shape having a specific length, and are arranged in parallel at a specific interval. First track slits 13a and 13b are formed on an upper surface of each of the first tracks 11a and 11b along a lengthwise direction of the first track 11a and 11b.

The first tracks 11a and 11b are provided with guide rails for a track 15a and 15b on the lower side of the first track slits 13a and 13b along the first track slits 13a and 13b.

Guide blocks for a track 17a and 17b connected to the second track 21 are reciprocally coupled to the guide rails for a track 15a and 15b. Track guide pins 23, which will be described below, are coupled to the guide blocks for a track 17a and 17b.

The second track 21 has a hollow bar shape having a specific length, and are arranged to be perpendicular to the first tracks 11a and 11b.

The track guide pins 23 protrude from the second track 21 at opposite ends of the second track 21. The track guide pins 23 pass through the first track slits 13a and 13b and are supported by the guide blocks for a track 17a and 17b.

Accordingly, the second track 21 is guided by the guide blocks for a track 17a and 17b connected to the track guide pins 23 to reciprocate along the guide rails for a track 15a and 15b. That is, the second track 21 is movably connected to the pair of first tracks 11a and 11b.

A second track slit 25 is formed on an upper surface of the second track 21 along a lengthwise direction of the second track 21.

The second track 21 is provided with a guide rail for a holder 27 on the lower side of the second track slit 25 along the second track slit 25.

A guide block for a holder 29 connected to a hand holder 31 is reciprocally coupled to the guide rail for a holder 27. A guide pin for a holder 45, which will be described below, is coupled to the guide block for a holder 29.

Here, the pair of first tracks 11a and 11b and the second track 21 are telescopically coupled, and for example, the tracks 11a, 11b, and 21 are retractably manufactured so that the lengths thereof may be adjusted to be extended or contracted.

The hand holder 31 is movably provided in the second track 21, and a hand and an arm of the user is held on the hand holder 31. The hand holder 31 includes a holder body 33, a knob 35, a support bracket 37, and a guide pin for a holder 45.

The holder body 33 has an arch-shaped cross-sectional shape that partially surrounds the arm of the user to hold the arm of the user.

The knob 35 has a rod shape, and is gripped by the hand of the user held on the holder body 33.

The support bracket 37 has a plate shape, and is moved along an upper surface of the second track 21. The support bracket 37 supports the knob 35 and the holder body 33 which are spaced apart from each other by an interval. The knob 35 and the holder body 33 are arranged transversely with respect to a lengthwise direction of the second track 21, and reciprocate along the lengthwise direction of the second track 21.

The guide pin for a holder 45 protrudes from the bottom of the support bracket 37. The guide pin for a holder 45 passes through the second track slit 25 and is supported by the guide block for a holder 29.

Accordingly, the hand holder 31 is guided by the guide block for a holder 29 connected to the guide pin for a holder 45 to reciprocate along the guide rail for a holder 27. That is, the hand holder 31 is movably connected to the second track 21.

Meanwhile, a slot 39 is formed in the support bracket 37 along a lengthwise direction of the support bracket 37.

Further, the holder body 33 is coupled to be movable along the slot 39 by a coupling member 41 provided on the bottom of the holder body 33.

In this way, because the slot 39 is formed in the support bracket 37 and the holder body is coupled to be movable along the slot 39 by the coupling member 41, an interval between the holder body 33 and the knob 35 may be freely adjusted.

Accordingly, the interval between the knob 35 and the holder body 33 may be variably adjusted according to the body condition of the user while the user performs rehabilitation training.

The stopper is provided in the second track 21 to limit movement of the second track 21 and the hand holder 31.

In the embodiment, the stopper includes a stopper for a track 51 and a stopper for a holder 61.

The stopper for a track 51 is provided in the first tracks 11a and 11b to limit movement of the second track 21. In the embodiment, the stopper for a track 51 includes a plurality of mounting grooves for a track 53 and a stopper pin for a track 55.

The mounting grooves for a track 53 are formed in the pair of first tracks 11a and 11b at an interval along the first track slits 13a and 13b, for example, along the movement path of the second track 21.

The stopper pin for a track 55 is selectively mounted on the plurality of mounting grooves for a track 53 to interrupt and release the movement path of the second track 21.

Figure 5:
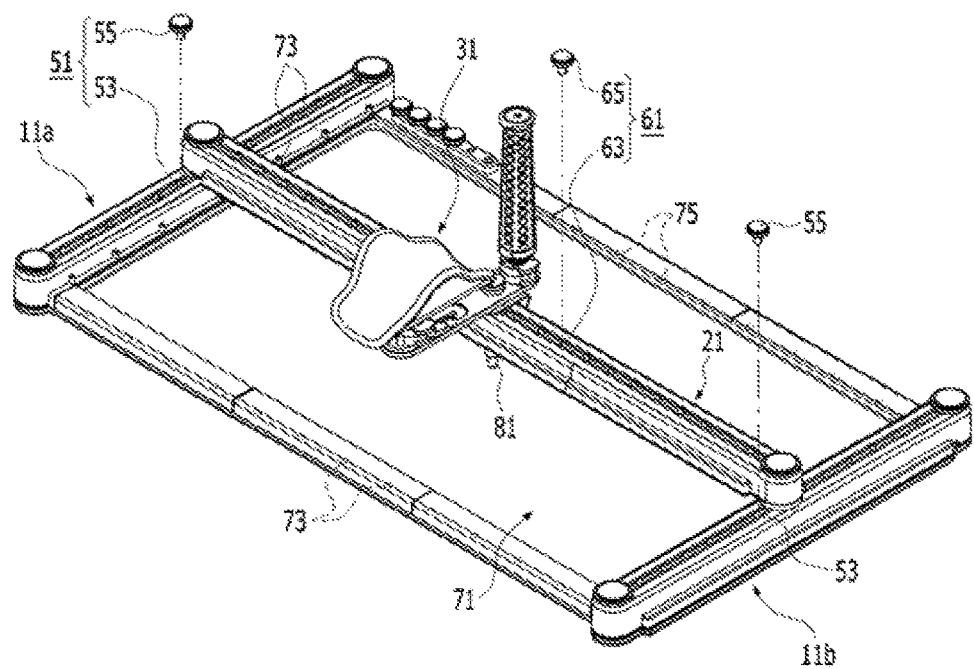
FIGS. 5 and 6 are views illustrating a process of limiting movement paths of the second track and the hand holder in the rehabilitation training apparatus of FIG. 1 as an embodiment.
Figure 6:
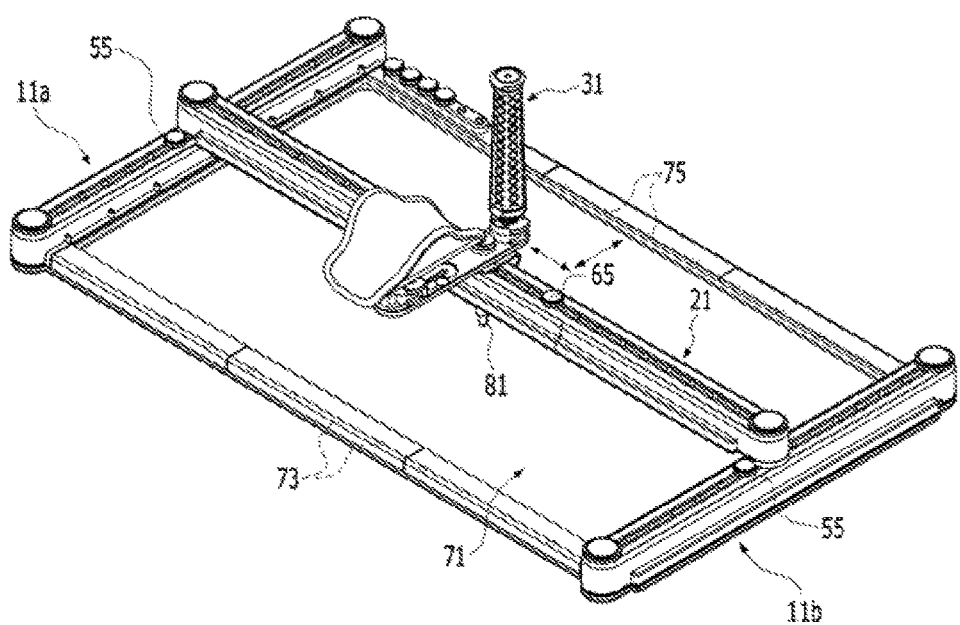

Accordingly, as illustrated in FIGS. 5 and 6, the stopper pin for a track 55 is mounted on at least one of the plurality of mounting grooves for a track 53 of the first tracks 11a and 11b, and the user may perform rehabilitation training while limiting the movement path of the second track 21 with respect to the first tracks 11a and 11b, for example, conveniently setting an exercise range of the user according to the body state of the user.

Figure 7:
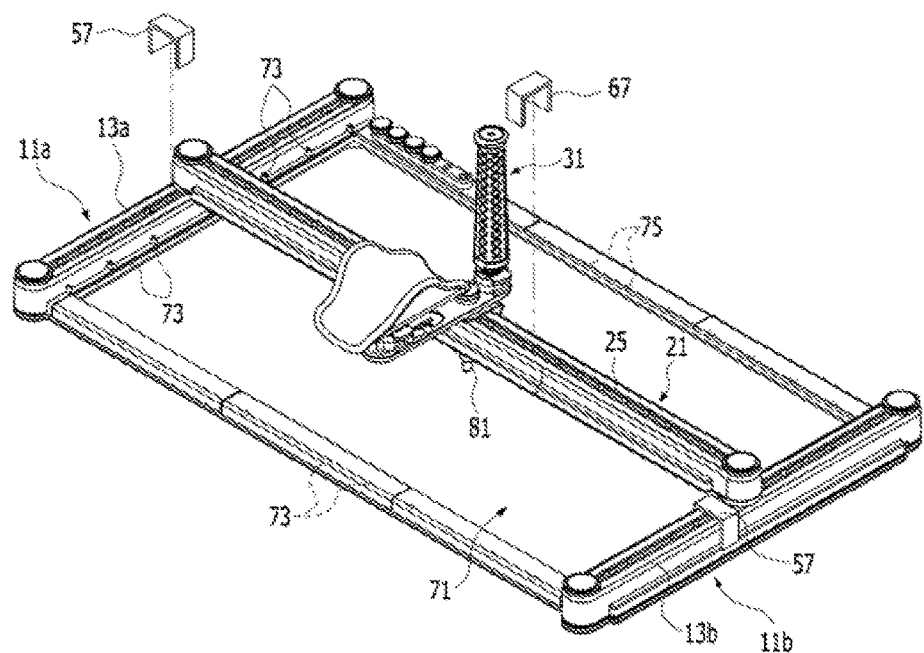
FIG. 7 is a view illustrating a process of limiting movement paths of the second track and the hand holder in the rehabilitation training apparatus of FIG. 1 as another embodiment.

Here, as illustrated in FIG. 7, the movement path of the second track 21 may be interrupted and released by mounting, instead of the mounting grooves for a track 53 and the stopper pin for a track 55 as the stopper for a track 51, a clip 57, for example, a clip 57 having a U-shaped cross-sectional shape having elasticity on the upper surfaces of the first tracks 11a and 11b.

The stopper for a holder 61 is provided in the second track 21 to limit the movement of the hand holder 31. The stopper for a holder 61 includes a plurality of mounting grooves for a holder 63 and a stopper pin for a holder 65.

The plurality of mounting grooves for a holder 63 are formed along the movement path of the hand holder 31, for example, along the first track slits 13a and 13b while being spaced apart from the second track at an interval.

The stopper pin for a holder 65 is selectively mounted on the plurality of mounting grooves for a holder 63 to interrupt and release the movement path of the hand holder 31.

Accordingly, as illustrated in FIGS. 5 and 6, the stopper pin for a holder 65 is mounted on at least one of the plurality of mounting grooves for a holder 63 of the second track 21, and the user may perform rehabilitation training while limiting the movement path of the hand holder 31 with respect to the second track 21, for example, conveniently setting an exercise range of the user according to the body state of the user.

Here, as illustrated in FIG. 7, the movement path of the second track 21 may be interrupted and released by mounting, instead of the mounting grooves for a holder 63 and the stopper pin for a holder 65 as the stopper for a holder 61, a clip 67, for example, a clip 67 having a U-shaped cross-sectional shape having elasticity on the upper surface of the second track 21. Further, although it is illustrated in the embodiment that the stopper for a track 51 and the stopper for a holder 61 are provided together as a stopper, the inventive concept is not limited thereto but may include only the stopper for a track 51 or the stopper for a holder 61 as a stopper.

Meanwhile, the rehabilitation training apparatus 10 according to the embodiment of the inventive concept may further include a board 71.

The board 71 has a rectangular plate shape such that the pair of first tracks 11a and 11b and the second track 21 form an X-Y coordinate plane, and is supported to the bottoms of the pair of first tracks 11a and 11b.

The pair of first tracks 11a and 11b are arranged in parallel at a pair of edges of the board 71, which face each other. The second track 21 is arranged across the plate surface of the board 71.

Hereinafter, for convenience of description, a direction in which the second track 21 is arranged will be referred to as the X axis direction and a direction in which the pair of first tracks 11a and 11b are arranged will be referred to as the Y axis direction.

Meanwhile, a plurality of light emitting elements 73 that emit light are provided at one X axis edge of the pair of X axis edges of the board 17, which face each other, along the lengthwise direction of the one X axis edge at an interval, and a plurality of light receiving elements 75 that receive light, which the plurality of light emitting elements 73 emit, are provided at an opposite X axis edge along the lengthwise direction of the opposite X axis edge at an interval. Accordingly, a plurality of linear X axis light paths are formed by the plurality of light emitting elements 73 provided at the one X axis edge and the plurality of light receiving elements 75 provided at the opposite X axis edge, and a plurality of X axis coordinate planes are formed in the board 71 by the plurality of X axis light paths.

Further, a plurality of light emitting elements 73 that emit light are provided at one Y axis edge of the pair of Y axis edges of the board 17, which face each other, along the lengthwise direction of the one Y axis edge at an interval, and a plurality of light receiving elements 75 that receive light, which the plurality of light emitting elements 73 emit, are provided at an opposite Y axis edge along the lengthwise direction of the opposite Y axis edge at an interval. Accordingly, a plurality of linear Y axis light paths are formed by the plurality of light emitting elements 73 provided at the one Y axis edge and the plurality of light receiving elements 75 provided at the opposite Y axis edge, and a plurality of Y axis coordinates are formed in the board 71 by the plurality of Y axis light paths.

Accordingly, because the plurality of light emitting elements 73 and the plurality of light receiving elements 75 are arranged along the Wedges of the board 71, the paths of the light formed by the plurality of light emitting elements 73 and the plurality of light receiving elements 75 form a plurality of X-Y axis coordinate planes while crossing each other.

Here, the light irradiated from the light emitting elements 73 to the light receiving elements 75 may be an infrared ray or a laser beam.

Further, the rehabilitation training apparatus 10 according to the embodiment of the inventive concept may further include a pointer 81.

The pointer 81 is provided on the hand holder 31, and indicates a location of the hand holder 31 on the X-Y axis coordinate plane of the board 71 by interrupting the path of light.

The pointer 81 includes a pointer tip 83, a tip holder 85, and a mount 87.

The pointer tip 83 interrupts the path of light while moving along the plate surface of the board 71. Here, the pointer tip 83 may slide along the plate surface of the board 71, or may move along the plate surface of the board 71 while being spaced apart from the plate surface of the board 71.

The tip holder 85 accommodates the pointer tip 83 such that the point tip 83 may be elevated so that the pointer tip 83 is attached to the plate surface of the board 71.

The mount 87 supports the tip holder 85 on the hand holder 31.

Accordingly, as the hand holder 31 moves along the X-Y axis coordinate plane of the board 71, the pointer tip 83 supported by the hand holder 31 indicates a location of the hand holder 31 on the X-Y axis coordinate plane of the board 71 by interrupting any one of the plurality of light paths formed in the board 71.

Further, because the pointer tip 83 is provided in the tip holder 85 to be elevated, the pointer tip 83 is accommodated in the tip holder 85 while absorbing an impact even when the arm or hand of the user is inclined toward the board 71 so that the user may do exercise while smoothly moving the hand holder 31.

Further, the rehabilitation training apparatus 10 according to the embodiment of the inventive concept may further include a communication module 91 that transmits the coordinate data obtained after the hand holder 31 is moved to an external device.

In this way, because the communication module 91 is provided, an amount of exercise and a state of the exercise may be conveniently recognized even in a remote site by transmitting movement data generated as the user moves the hand holder 31, for example, movement path data of the hand holder 31 on the X-Y axis coordinate plane of the board 71 to the external device in real time.

With this configuration, the user may perform rehabilitation training while changing angles of the joints of the wrist and the shoulder of the user, by freely moving the hand holder 31 on the X-Y axis coordinate plane of the board 71 with a force, for example, by moving the hand holder 31 in a desired direction by using a fine muscular force.

Then, the movement path data of the hand holder 31, for example, the coordinate data obtained after the pointer 81 is moved may be transmitted to the external device in real time through the communication module 91, and accordingly, the amount of the exercise of the user and the state of the exercise may be conveniently recognized even from a remote site.

Meanwhile, as another exercise method of the rehabilitation training apparatus 10 according to the embodiment of the inventive concept, after the user holds a hand and an arm on the hand holder 31 in a state in which pattern data containing a specific pattern is displayed through a display around the rehabilitation training apparatus 10, the user performs rehabilitation training while changing the angles of the joints of the wrist and the shoulder of the user by moving the hand holder 31 on the X-Y axis coordinate plane of the board 71 according to the pattern data, for example, by moving the hand holder 31 by using a fine muscular force while watching the pattern data displayed through the display.

Then, the user may recognize the rehabilitation training state of the user by comparing the movement path data of the hand holder 31, for example, the coordinate data obtained after the point 81 is moved, and the pattern data displayed on the display.

In this way, according to the inventive concept, the user may perform rehabilitation training while conveniently setting an exercise range according to the body state of the user by movably disposing the second track in the pair of first tracks arranged in parallel while the second track is spaced apart from the first tracks at an interval, by reciprocating the hand holder on which a hand of the user is held along the second track and reciprocating the second track along the first tracks, and by providing the stopper that limits the movements of the second track and the hand holder, and may perform rehabilitation training while changing the angles of the joints of the wrist and the shoulder of the user by moving a hand and an arm by using the muscular force of the user.

Meanwhile, although it has been described in the above-mentioned embodiment that the board is horizontally held on the bottom, the inventive concept is not limited thereto, and a support that is perpendicular to the bottom or hinge-coupled to the bottom of the board to be foldable may be mounted on one edge of the board such that the board may be held to be inclined with respect to the bottom. In this way, because the hand holder has to be moved with a force that is stronger than in the state in which the board is horizontally held on the bottom as the board is held on the bottom to be inclined, the amount of exercise of the user may be enhanced.

According to the inventive concept, the user may perform rehabilitation training while conveniently setting an exercise range according to the body state of the user, and may perform rehabilitation training while changing the angles of the joints of the wrist and the shoulder of the user, by moving the hand and the arm by using the muscular force of the user.

Further, rehabilitation training may be performed by moving a hand holder in which a hand of the user is held according to characteristics of the user in various patterns and changing the angles of the joints of a wrist and a shoulder of the user.

While the inventive concept has been described with reference to embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A rehabilitation training apparatus comprising:
   a pair of first tracks that are arranged in parallel at an interval;
   a second track movably connected to the pair of first tracks;
   a hand holder that is movably provided in the second track and on which at least one of a hand and an arm of a user is held; and
   a stopper for a track provided in the first tracks to limit movements of the second track, and
   wherein the stopper for a track includes:
   a plurality of mounting grooves for a track formed in the pair of first tracks along a movement path of the second track at an interval; and
   a stopper pin for a track selectively mounted on the plurality of mounting grooves for a track to interrupt and release the movement path of the second track.

2. A rehabilitation training apparatus comprising:
   a pair of first tracks that are arranged in parallel at an interval;
   a second track movably connected to the pair of first tracks;
   a hand holder that is movably provided in the second track and on which at least one of a hand and an arm of a user is held; and
   a stopper for a track provided in the first tracks to limit movements of the second track, and
   wherein the stopper for a track includes a plurality of clips mounted on the pair of first tracks to interrupt and release the movement path of the second track.

3. The rehabilitation training system of claim 1, further comprising:
   a stopper for a holder provided in the second track to limit the movement of the hand holder.

4. The rehabilitation training system of claim 3, wherein the stopper for a holder includes:
   a plurality of mounting grooves for a holder formed in the second track along the movement path of the hand holder at an interval; and
   a stopper pin for a holder selectively mounted on the plurality of mounting grooves for a holder to interrupt and release the movement path of the hand holder.

5. The rehabilitation training system of claim 3, wherein the stopper for a holder includes a plurality of clips mounted in the movement path of the hand holder of the second track to interrupt and release the movement path of the hand holder.

6. A rehabilitation training apparatus comprising:
   a pair of first tracks that are arranged in parallel at an interval;
   a second track movably connected to the pair of first tracks;
   a hand holder that is movably provided in the second track and on which at least one of a hand and an arm of a user is held;
   a stopper for a track provided in the first tracks to limit movements of the second track;
   a board having a rectangular plate shape and forming an X-Y coordinate plane formed by the pair of first tracks and the second track;
   a plurality of light emitting elements that emit light; and
   a plurality of light receiving elements that receive light emitted from the plurality of light emitting elements, and
   wherein paths of the light, which are formed by the plurality of light emitting elements and the plurality of light receiving elements, form an X-Y axis coordinate plane in the board while crossing each other.

7. The rehabilitation training system of claim 6, further comprising:
   a pointer provided on the hand holder to indicate a location of the hand holder on the X-Y axis coordinate plane of the board by interrupting the paths of the light.

8. The rehabilitation training system of claim 7, wherein the pointer includes:
   a pointer tip that interrupts the paths of the light while moving along a plate surface of the board;
   a tip holder in which the pointer tip is accommodated to be elevated such that the pointer tip is attached to the plate surface of the board; and
   a mount that supports the tip holder on the hand holder.

9. The rehabilitation training system of claim 6, further comprising:
   a communication module that transmits coordinate data obtained after the hand holder is moved to an external device.

10. The rehabilitation training system of claim 1, wherein the hand holder includes:
    a holder body on which an arm of the user is held;
    a knob gripped by the hand of the user held on the holder body;
    a support bracket that supports the knob and the holder which are spaced apart from each other at an interval; and
    a guide pin for a holder coupled to the support bracket to guide the support bracket such that the support bracket reciprocates along the second track.

11. The rehabilitation training system of claim 10, further comprising:
    a slot formed in the support bracket; and
    a coupling member that couples the holder body to the slot such that the holder body is movable.

12. The rehabilitation training system of claim 1, further comprising:
    a pair of guide rails for a track arranged in the pair of first tracks along the pair of first tracks; and
    a pair of guide blocks for a track, to which the second track is connected, and which reciprocates along the pair of guide rails for a track.

13. The rehabilitation training system of claim 1, further comprising:
    a guide rail for a holder that is arranged along the second track; and
    a guide block for a holder connected to the hand holder to reciprocate along the hand guide rail.

14. The rehabilitation training system of claim 2, further comprising:
    a stopper for a holder provided in the second track to limit the movement of the hand holder.

15. The rehabilitation training system of claim 2, wherein the hand holder includes:
    a holder body on which an arm of the user is held;
    a knob gripped by the hand of the user held on the holder body;
    a support bracket that supports the knob and the holder which are spaced apart from each other at an interval; and
    a guide pin for a holder coupled to the support bracket to guide the support bracket such that the support bracket reciprocates along the second track.

* * * * *